United States Patent
Briggs et al.

(10) Patent No.: US 10,946,116 B1
(45) Date of Patent: Mar. 16, 2021

(54) PHOTOCATALYTIC PANELS

(71) Applicant: Genesis Air, Inc., Lubbock, TX (US)

(72) Inventors: Daniel James Briggs, Lubbock, TX (US); Brandon Matthew Hawkins, Lubbock, TX (US)

(73) Assignee: GENESIS AIR, INC., Lubbock, TX (US)

(*) Notice: Subject to any disclaimer, the term of this patent is extended or adjusted under 35 U.S.C. 154(b) by 0 days.

(21) Appl. No.: 16/870,046

(22) Filed: May 8, 2020

Related U.S. Application Data

(60) Provisional application No. 62/949,346, filed on Dec. 17, 2019.

(51) Int. Cl.
| | | |
|---|---|---|
| *G01N 21/00* | (2006.01) | |
| *G01N 23/00* | (2006.01) | |
| *A61N 5/00* | (2006.01) | |
| *A61L 9/20* | (2006.01) | |
| *F24F 8/10* | (2021.01) | |
| *F24F 8/167* | (2021.01) | |

(52) U.S. Cl.
CPC ............ *A61L 9/205* (2013.01); *F24F 8/10* (2021.01); *A61L 2209/12* (2013.01); *A61L 2209/14* (2013.01); *A61L 2209/16* (2013.01); *F24F 8/167* (2021.01)

(58) Field of Classification Search
CPC ..... A61L 9/00; A61L 9/16; A61L 9/20; A61L 9/205; A61L 2209/00; A61L 2209/14; A61L 2209/15; A61L 2209/16; A61L 2209/22
USPC .............. 422/24; 250/454.11, 455.11, 492.1
See application file for complete search history.

(56) References Cited

U.S. PATENT DOCUMENTS

| | | | |
|---|---|---|---|
| 7,326,387 B2 * | 2/2008 | Arts .................... | A61L 2/10 422/186.3 |
| 2008/0031783 A1 * | 2/2008 | Briggs ................ | B01D 53/007 422/121 |

\* cited by examiner

*Primary Examiner* — Monzer R Chorbaji

(57) ABSTRACT

An air sanitation and purification photocatalytic panel includes a frame that has a photocatalytic scrim positioned within the frame and a plurality of UV light sources positioned within the frame proximate to the photocatalytic scrim. The frame is made of a metal and/or alloy. The photocatalytic scrim is a pleated structure. Each of the plurality of UV light sources are oriented towards the photocatalytic scrim. The photocatalytic scrim includes a substrate a photocatalytic coating adhered to the substrate. The frame and photocatalytic scrim are oriented parallel to each other. The UV light sources illuminate the photocatalytic coating and initiate a photocatalytic reaction therein. During operation, the panel is positioned perpendicular to the airstream such that the airstream is forced through the substrate.

7 Claims, 5 Drawing Sheets

AVAILABLE TUBE AREA

MAXIMUM ACTIVATION POTENTIAL USING SINGLE LIGHT

ASSEMBLY VIEW

PHOTOCATALYTIC PANELS

CROSS-REFERENCE TO RELATED APPLICATIONS

This application claims priority to U.S. Provisional Application No. 62/949,346 filed Dec. 17, 2019, which is hereby incorporated herein by reference.

FIELD OF THE INVENTION

The present disclosure relates generally to air sanitation and purification. More specifically, the present disclosure describes air sanitation and purification using photocatalytic panels.

BACKGROUND OF THE INVENTION

In the medical field, for instance, hospitals typically rely on sanitation to prevent infection of patients undergoing surgery. Given that a hospital, by its nature, has a large concentration of sick persons, air sanitation is desirable to minimize the risks of diseases being communicated to noninfected persons, both patients and staff. As per commercial use, air purification technologies are critical in a number of applications, including the remediation of indoor air pollutants, especially including organic solvents to which exposure has been determined to be harmful. Additionally, air purification and sanitation devices have applications in home use, particularly in the context of efforts to remediate water damage to property.

In such situations, for example, the damp conditions caused by water damage can result in the explosive growth of both bacteria and molds, with the entire building being contaminated by airborne bacteria and mold spores. In fact, mold spore contamination resulting from water damage, particularly with respect to the mold Stacybotrys chartarum, negatively impacts homeowners and insurers. For example, insurance companies annually lose billions of dollars on mold claims, which may result in insurance premiums increases or a cessation of business in many states.

Existing devices for sanitation and decontamination of air include deodorizers, chemical- and charcoal-based air scrubbers, ozone producers, simple filtration systems, ionization apparatus, and exhaust fans. These existing systems are typically dependent on existing environmental heating/air conditioning systems to provide air flow in order to treat large, multi-room volumes of air.

BRIEF DESCRIPTION OF THE DRAWINGS

Some of the embodiments will be described in detail, with reference to the following figures, wherein like designations denote like members, wherein.

Figure 1:
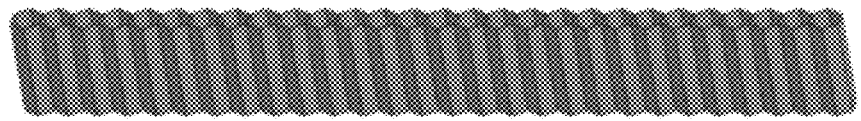
FIG. 1 illustrates the activation potential of a honeycomb assembly known in the art.
Figure 1:
Figure 1:
Figure 1:

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "dorsal" refers to positions that are located near, on, or towards the upper or top side of a structure.

The present disclosure includes many aspects and features. Moreover, while many aspects and features relate to, and are described in the context of detection of presence of one or more intruder devices, embodiments of the present disclosure are not limited to use only in this context.

In the medical field, for instance, hospitals typically rely on sanitation to prevent infection of patients undergoing surgery. Given that a hospital, by its nature, has a large concentration of sick persons, air sanitation is desirable to minimize the risks of diseases being communicated to noninfected persons, both patients and staff. As per commercial use, air purification technologies are critical in a number of applications, including the remediation of indoor air pollutants, especially including organic solvents to which exposure has been determined to be harmful. Additionally, air purification and sanitation devices have applications in home use, particularly in the context of efforts to remediate water damage to property.

In such situations, for example, the damp conditions caused by water damage can result in the explosive growth of both bacteria and molds, with the entire building being contaminated by airborne bacteria and mold spores. In fact, mold spore contamination resulting from water damage, particularly with respect to the mold Stacybotrys chartarum, negatively impacts homeowners and insurers. For example, insurance companies annually lose billions of dollars on mold claims, which may result in insurance premiums increases or a cessation of business in many states.

Existing devices for sanitation and decontamination of air include deodorizers, chemical- and charcoal-based air scrubbers, ozone producers, simple filtration systems, ionization apparatus, and exhaust fans. These existing systems are typically dependent on existing environmental heating/air conditioning systems to provide air flow in order to treat large, multi-room volumes of air.

This rapid sanitation will substantially reduce the costs associated with decontaminating premises that have sustained water damage, resulting in substantial savings to both property owners and insurance companies. For example, VOCs are emitted as gases from certain solids or liquids. VOCs include a variety of chemicals, some of which may have short- and long-term adverse health effects. Concentrations of many VOCs are consistently higher indoors (up to ten times higher) than outdoors. VOCs are emitted by a wide array of products numbering in the thousands.

FIG. 1 illustrates the activation potential of a honeycomb assembly known in the art. Traditional PCO installations position the UV lamps away from the catalyst (generally 15 cm), allowing most of that energy to be unused and wasted. For example, each honeycomb tube is oriented perpendicular to the UV light, which thereby allows only the honeycomb tube(s) closest to the UV light to receive the maximum amount of UV light compared to other tubes of the assembly and thereby the maximum activation potential.

Many PCO products are found to create intermediaries due to incomplete reduction reactions. This can be due to poor energy distribution, lack of irradiation due to shadowing, poorly activated $TiO_2$ or silica poisoning. The instant disclosure seeks to provide photocatalytic panels having an enhanced activation potential compared to solutions known in the art. The instant disclosure seeks to provide photocatalytic panels that exhibit improved the first-pass contaminant removal efficiency in an airstream contaminated with VOCs and biologicals.

Figure 2:
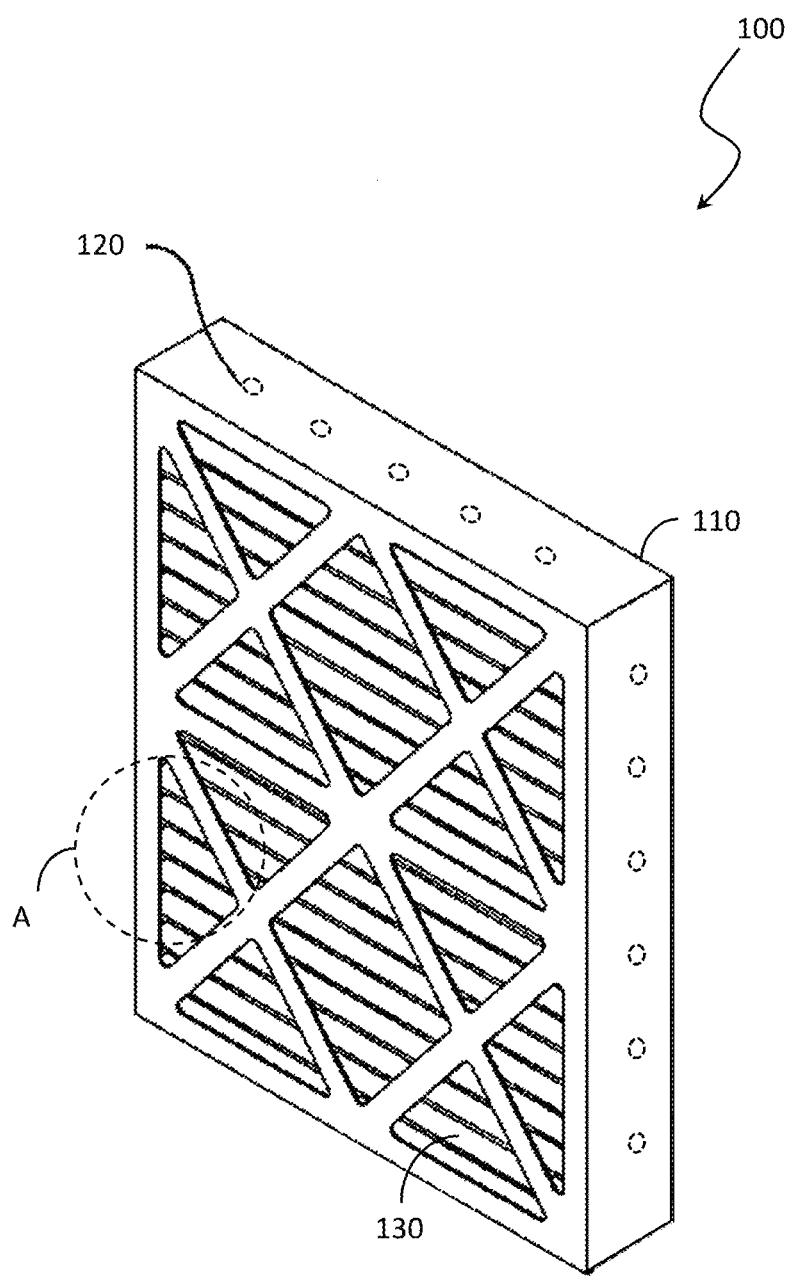
FIG. 2 depicts a photocatalytic panel according to some embodiments.

FIG. 2 depicts a photocatalytic panel, generally 100, according to some embodiments. The photocatalytic panel 100 includes photocatalytic scrim 130 and a plurality of UV light sources 120 each positioned within frame 110. The frame 110 is a rigid structure that the photocatalytic scrim 130 and the plurality of UV light sources 120 are positioned within. The frame 110 can include any material, feature, and/or number of components, as well as assume any shape and/or orientation to fulfill one or more embodiments disclosed herein. The frame 110 is preferably a hollow rectangular shape to allow the photocatalytic panel 100 to be positioned within an airduct. In other embodiments, the frame 110 has an overall structure that complements the interior of an airduct. The frame 110 is formed using a metal(s), alloy(s), and/or other heat-resistant materials.

Each of the UV light sources 120 are internally positioned along the center of the frame 110 and integrated therein, which thereby illuminates the photocatalytic scrim 130 in its entirety as opposed to its leading edge (e.g., as experienced with honeycomb assemblies). Although each of the UV light sources 120 can utilize any range of UV light, they preferably utilize germicidal UV light (e.g., 100-280 nm), which has germicidal properties. The plurality of UV light sources 120 most preferably utilize 254 nm UV light. The UV light serves as an energy source to create hydroxy radicals. The plurality of UV light sources 120 are positioned within the frame 110 proximate to and oriented towards the photocatalytic scrim 130.

Figure 3:
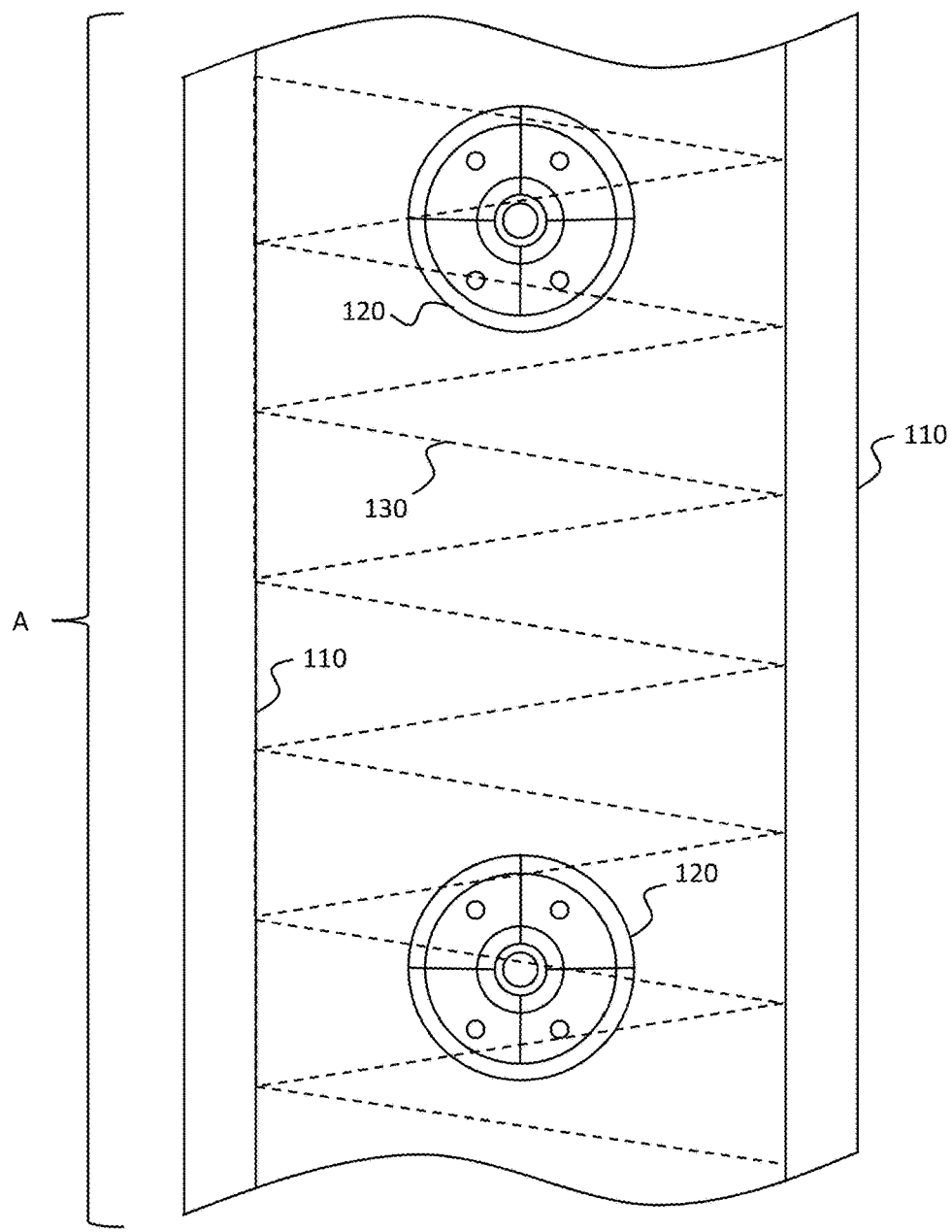
FIG. 3 illustrates a side view of Area A of FIG. 1 according to some embodiments.
Figure 3:
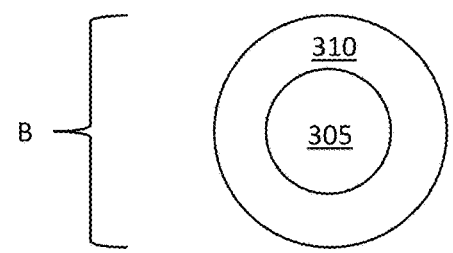

The photocatalytic panel 100 attains its efficiency from the use of the photocatalytic scrim 130 incorporated therein. The photocatalytic scrim 130 is preferably a pleated structure to increase the amount of irradiated surface area and increase the residence time a contaminant experiences. The photocatalytic scrim 130 is preferably a woven material. The photocatalytic scrim 130 includes a substrate 305 and a photocatalytic coating 310 adhered thereto (FIG. 3). Applicable substrate materials include, but are not limited to metal plate, metal wire, ceramic substrates, and glass substrates (including fiberglass). According to preferred embodiments the substrate 305 is a woven material (e.g., a woven fiberglass fabric). The weave of the fiberglass allows folding of the fabric into complex shapes as desired, including pleats or rolls.

Not to be limited by theory, issues associated with loss of the photocatalytic coating 310 from the surface of the substrate 305 are alleviated through the use of the photocatalytic coating 310, which preferably includes $TiO_2$ and an organic polymer binder that is substantially transparent to ultraviolet light. $TiO_2$ can be present at any concentration, weight %, etc. that fulfills the intentions of one or more embodiments disclosed herein. The $TiO_2$ is preferably present at 0.5-20% of the total weight of the photocatalytic scrim 130. $TiO_2$ particles preferably have a 20-100 nm diameter. Photocatalytic coating 310 can include any components and/or be present at any thickness that fulfills the intentions of one or more embodiments disclosed herein. Photocatalytic coating 310 preferably has a thickness of 10 nm to $9.8 \times 10^4$ nm. The organic polymer is translucent to ultraviolet light to allow the plurality of UV light sources 120 to initiate a photocatalytic reaction with the photocatalytic coating 310.

The photocatalytic reaction is initiated when a photoexcited electron is promoted from the filled valence band of a photocatalytic coating 310 (SC) to the empty conduction band as the absorbed photon energy, hv, equals or exceeds the band gap of the $TiO_2$, leaving behind a hole in the valence band. In concert, electron and hole pair (e--h+) is generated. The following chain reactions have been widely accepted:

$$TiO_2 + hv \rightarrow e^- + h^+ \quad (1)$$

$$OH^- + h^+ \rightarrow .OH \quad (2a)$$

$$H_2O + h^+ \rightarrow H^+ + .OH \quad (2b)$$

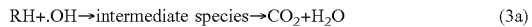
$$RH + .OH \rightarrow \text{intermediate species} \rightarrow CO_2 + H_2O \quad (3a)$$

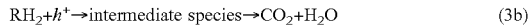
$$RH_2 + h^+ \rightarrow \text{intermediate species} \rightarrow CO_2 + H_2O \quad (3b)$$

In preferred embodiments, the woven material of the substrate 305 is about 50% occluded by the photocatalytic coating 310, which allows the photocatalytic panel 101 to have a reduced effect on pressure drop (e.g., 0.05" $H_2O$ at 500 fpm. FIG. 3 illustrates a side view of Area A of FIG. 1 according to some embodiments. The frame 110 and the photocatalytic scrim 130 are preferably oriented parallel to each other.

Not to be limited by theory, first pass efficiency (e.g., a measure of the effectiveness of a process and the elimination of waste from that process) is improved by increasing the available surface area of the photocatalytic coating 310 without restricting airflow. The pleated structure of the photocatalytic scrim 130 increases the residence time that contaminants experience by increasing the depth of the photocatalytic coating 310 (i.e. the photocatalyst) in the direction of airflow. For example, as the depth of the pleat increases (e.g., to 6"), the residence time a contaminant experienced increases. A 1" honeycomb monolith has a min residence time of 0.265 seconds at 500 fpm, while the 6" pleated catalyst has a minimum residence time of 0.72 seconds at 500 fpm. In some embodiments, the photocatalytic scrim 130 is a 2-6" pleated structure having 1-2 pleats per inch.

The efficiency the UV light sources 120 increases when relocated within the catalyst and therefore uses the most intense portions of the lamp curve. For example, the plurality of UV light sources 120 are preferably positioned up to 4" from the photocatalytic scrim 130. For example, each UV light source 130 may be positioned about 6" from adjacent UV light sources 130. The plurality of UV light sources 130 can achieve at least 1.5 mW/cm2.

Figure 4:
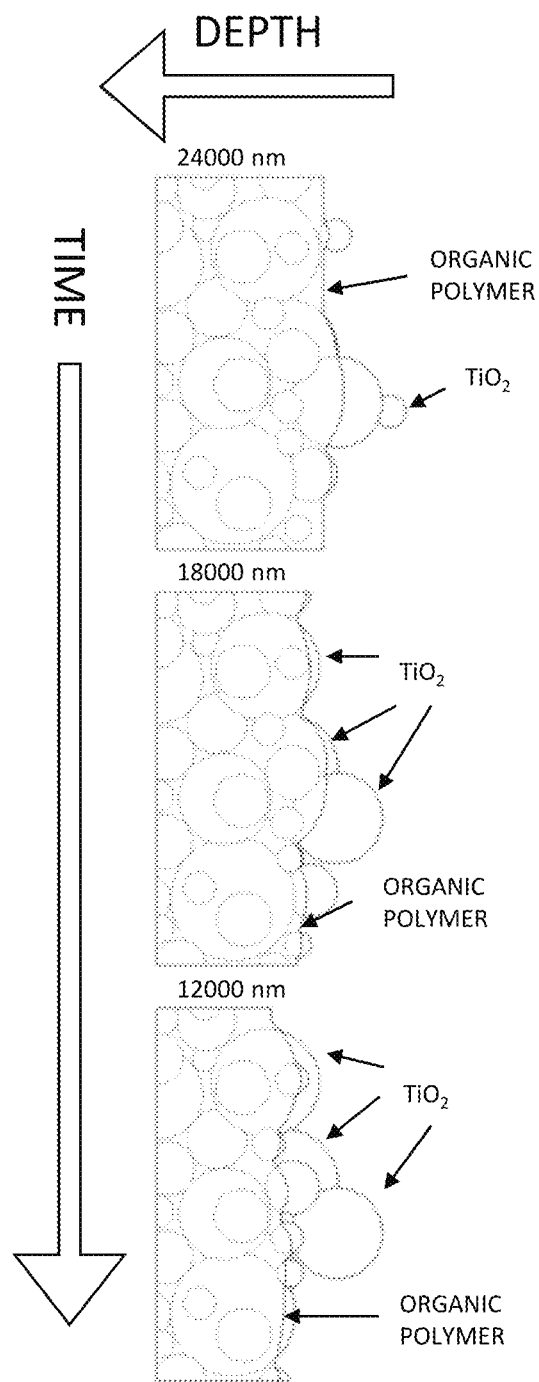
FIG. 4 illustrates the self-renewing mechanism of the photocatalytic coating according to some embodiments.

FIG. 4 illustrates the self-renewing mechanism of the photocatalytic coating 310 according to some embodiments. As shown, fresh $TiO_2$ is exposed as the photocatalytic coating 310 (e.g., the organic polymer) shrinks from 24.00 nm to 12,000 nm over time. The photocatalytic coating 310 is photoreactive and energizes new $TiO_2$ crystals over time. The photocatalytic coating 310 is energized by the plurality of UV light sources 130. The reenergizing feature allows the photocatalytic coatings 310 to potentially have up to a 15-year service life.

Figure 5:
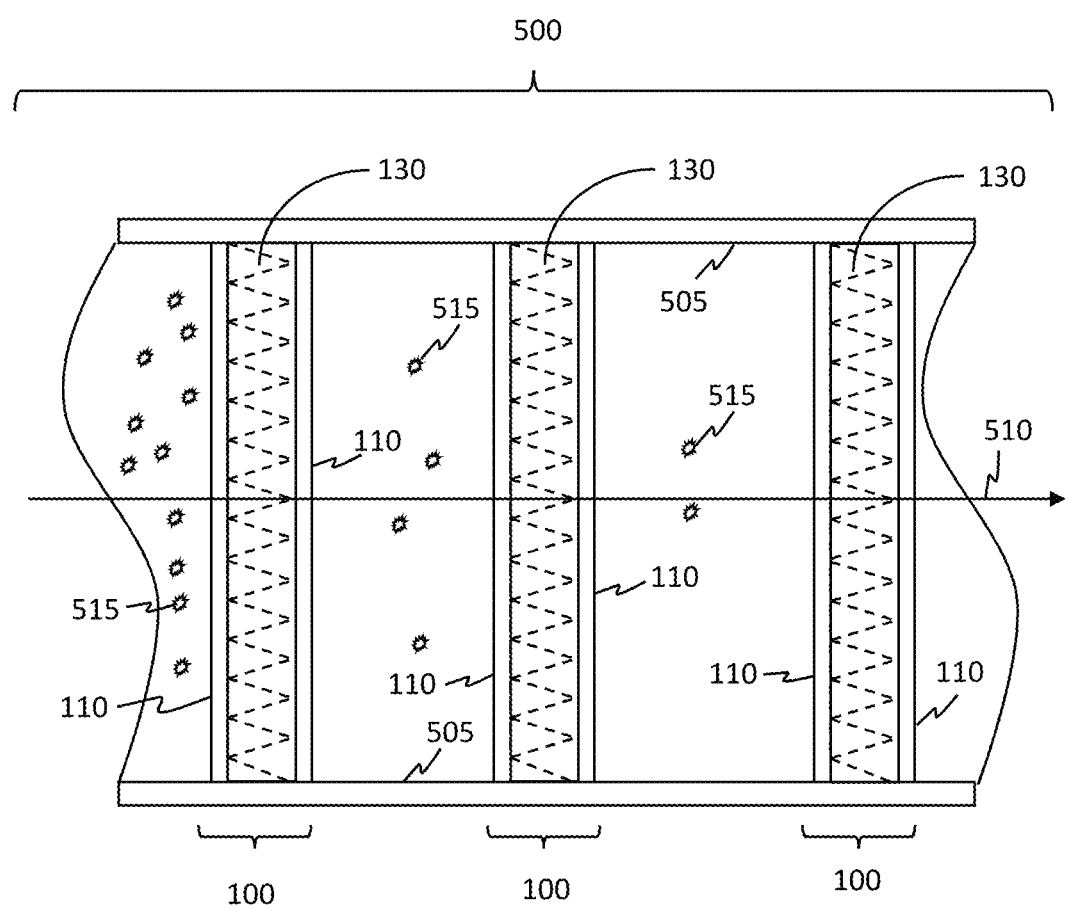
FIG. 5 illustrates an air sanitation system that includes several photocatalytic panel according to some embodiments.

FIG. 5 illustrates an air sanitation system, generally 500, that includes several photocatalytic panel according to some embodiments. Here, air sanitation system 500 includes airduct 505, which may have any cross-section shape that facilitates the sanitation of airstream 510. Specifically, the section of the air sanitation system 500 includes three of the photocatalytic panels 100 positioned perpendicular to the airstream 510 such that the airstream 510 is forced through the substrate 305. The airstream 510 contains contaminants 515 (e.g., VOCs; organic compounds, including bacteria, mold spores, viruses, and other organisms; dust mites, house dust, bacteria, pet dander and many other submicroscopic poisons, allergens and irritants). The airstream 510 flows through the photocatalytic panels 100 and interacts with the reactive oxygen species (hydroxyl radicals) of the photocatalytic coatings 310 thereby reducing the amount of the contaminants 515 in the airstream 510.

Each of the photocatalytic panels 100 filters out a portion of the contaminants 515. Any number of the photocatalytic panels 100 may be utilized to remove contaminants 515 from an airstream (e.g., the airstream 510). In other words, the photocatalytic panels 100 are scalable and may be used in, for example, large commercial heating, ventilation and air conditioning ("HVAC") systems, small residential HVAC units (e.g., blower fed HVAC units), and HVAC units that include all components (e.g., air movement capabilities) in a self-contained unit that has its own air movement capability (e.g., unit sized to regulate spaces apart from the HVAC system).

Although the disclosure has been explained in relation to its preferred embodiment, it is to be understood that many other possible modifications and variations can be made without departing from the spirit and scope of the disclosure.

What is claimed is:
1. A photocatalytic panel comprising:
   a frame;
   a photocatalytic scrim;
   the photocatalytic scrim being positioned within the frame;
   a plurality of UV light sources;
   the plurality of UV light sources being positioned within the frame;
   the plurality of UV light sources being proximate to the photocatalytic scrim;

an arbitrary UV light source among the plurality of UV light sources being positioned about 6 inches from an adjacent UV light source among the plurality of UV light sources;

the frame comprising a metal and/or an alloy;

the photocatalytic scrim being a pleated structure;

each of the plurality of UV light sources being oriented towards the photocatalytic scrim;

the photocatalytic scrim comprising a substrate and a photocatalytic coating;

the photocatalytic coating being adhered to the substrate;

the photocatalytic coating comprising a thickness of 10 nm to $9.8\times10^4$ nm;

the frame and the photocatalytic scrim are oriented parallel to each other;

the plurality of UV light sources initiating a photocatalytic reaction with the photocatalytic coating; and the photocatalytic panel being configured to be positioned perpendicular to an airstream such that the airstream is forced through the substrate.

2. The photocatalytic panel of claim 1, wherein the photocatalytic coating comprises $TiO_2$ and an organic polymer.

3. The photocatalytic panel of claim 2, wherein the $TiO_2$ is 0.5-20% of the total weight of the photocatalytic scrim.

4. The photocatalytic panel of claim 2, wherein the organic polymer is translucent to ultraviolet light.

5. The photocatalytic panel of claim 2, wherein the $TiO_2$ comprises a 20-100 nm diameter.

6. The photocatalytic panel of claim 1, wherein the substrate comprises a woven fiberglass fabric.

7. The photocatalytic panel of claim 1, wherein the substrate is a woven material that is about 50% occluded by the photocatalytic coating.

* * * * *